United States Patent [19]

Pullan

[11] Patent Number: 4,922,181

[45] Date of Patent: May 1, 1990

[54] APPARATUS FOR MONITORING THE DIELECTRIC CONSTANT OF AN ARTICLE

[75] Inventor: Brian R. Pullan, Stockport, England

[73] Assignee: Laetus Systems Limited, Cambridge, England

[21] Appl. No.: 227,274

[22] Filed: Aug. 2, 1988

[30] Foreign Application Priority Data

Aug. 6, 1987 [GB] United Kingdom ............... 8718606

[51] Int. Cl.$^5$ ............................................. G01R 27/26
[52] U.S. Cl. ................................. 324/664; 324/690
[58] Field of Search ............. 324/61 R, 61 P, 57 R, 324/60 C, 60 R, 551, 554, 557–559; 341/15; 340/870.37

[56] References Cited

U.S. PATENT DOCUMENTS

| | | | |
|---|---|---|---|
| 3,391,337 | 7/1968 | Preikschat | 324/61 R |
| 3,497,802 | 2/1970 | Biddle | 324/61 R |
| 3,519,922 | 7/1970 | Nash et al. | 324/61 R |
| 3,815,021 | 6/1974 | Kerr | 324/61 R |
| 4,031,752 | 6/1977 | Sanders | 73/159 |
| 4,190,797 | 2/1980 | Lecklider et al. | 324/61 R |
| 4,322,678 | 3/1982 | Capots et al. | 324/61 R |
| 4,377,783 | 3/1983 | Wagner | 324/61 |
| 4,471,295 | 9/1984 | Vermeiren | 324/61 R |
| 4,733,166 | 3/1988 | Wagner | 324/61 R |
| 4,752,727 | 6/1988 | Schneider | 324/61 P |

FOREIGN PATENT DOCUMENTS 2150304  6/1985  United Kingdom .

OTHER PUBLICATIONS

*NASA Tech Brief, Dielectric Scanning Locates Voids in Glass Foam,* National Aeronautics and Space Administration, Sep., 1984, No. 9.

*Primary Examiner*—Gerald R. Strecker
*Assistant Examiner*—Jack B. Harvey
*Attorney, Agent, or Firm*—Jeffers, Hoffman & Niewyk

[57] ABSTRACT

Apparatus for monitoring the dielectric composition of articles, particularly articles such as blisterpacks and laminated boards. The apparatus comprises an amplifying circuit including a capacitor between the electrodes (1, 3) of which an article (22) is moved in use. The gain of the amplifying circuit varies with the capacitance of the capacitor so that the amplifying circuit provides an output signal, the peak value of the output signal varying with the dielectric constant of the article (22) between the capacitor electrodes (1, 3). Typically the amplifying circuit includes an operational amplifier (9) the non-inverting input (10) of which is connected to a ground potential (6) and the inverting input (8) is connected to one electrode (3) of the capacitor. A feedback loop (11) is applied between the output (14) of the operational amplifier (9) and the inverting input (8) of the operational amplifier to force the inverting input to the same potential as the non-inverting input. Typically an oscillating signal source (5) is connected to the other electrode (1) of the capacitor.

14 Claims, 4 Drawing Sheets

APPARATUS FOR MONITORING THE DIELECTRIC CONSTANT OF AN ARTICLE

FIELD OF THE INVENTION

This invention relates to monitoring apparatus and in particular apparatus for monitoring the dielectric constant of an article.

DESCRIPTION OF THE PRIOR ART

Previous methods of monitoring the dielectric composition of an article have measured changes in capacitance of a capacitor as the dielectric constant between the capacitor electrodes changes. In order to measure the changes in capacitance these previous methods have used complex a.c. bridge circuits. This method of monitoring the dielectric constant results in equipment which is complicated to use and which is susceptible to stray capacitances. An example of such a method is described in GB-A-No. 2148498.

SUMMARY OF THE INVENTION

In accordance with the present invention I provide monitoring apparatus which comprises an amplifying circuit including a capacitor between the electrodes of which an article is moved in use and in which the gain of the amplifying circuit varies with the capacitance of the capacitor so that the peak value of the output signal of the amplifying circuit varies with the dielectric constant of the article between the capacitor electrodes.

In the preferred arrangement we use a simple amplifying circuit including for example an operational amplifier with one of the inputs at a constant electrical potential and the other input connected to one electrode of the capacitor so that changes in dielectric constant between the capacitor plates affect the gain of the amplifier. The peak output values from the amplifier are found to vary with the dielectric constant between the capacitor electrodes and as one input of the operational amplifier is kept at a constant potential stray capacitances have minimal effect on the output signals from the amplifiers.

Preferably, the amplifying circuit includes an operational amplifier with the non-inverting input connected to a constant electrical ground potential and the inverting input connected to one electrode of the capacitor. Typically a feedback loop is present between the operational amplifier output and the inverting input. This has the effect of forcing the inverting input to the same potential as the non-inverting input, usually ground.

The advantage of using this technique is that the capacitor electrode connected to the inverting input remains at a constant potential and therefore the electric field between the capacitor plates remains substantially constant.

In addition a guard electrode would typically surround the capacitor electrode connected to the inverting input and would be maintained at substantially the same constant potential. This has the advantage of helping to maintain a substantially uniform electric field over the area of the article being monitored.

Typically an oscillating voltage signal is applied to the capacitor electrode not connected to the operational amplifier.

Preferably, a peak detecting circuit is also provided which receives the output signals from the amplifying circuit and outputs the peak values of the signals received from the amplifying circuit.

In one embodiment a plurality of amplifying circuits and peak detector circuits are provided, the respective capacitors being positioned in a line transverse to the direction of movement of an article in use, the apparatus further comprising a multiplexer to which output signals from the peak detector circuits are sent. Typically the multiplexer will then feed each signal in turn to a processing unit and after processing the signals are displayed.

Although it would be possible to provide a compensation device if amplifying circuits with different gains were used each amplifying circuit preferably has substantially the same gain when the capacitance of each of the respective capacitors is substantially equal.

In addition, the constant electric potential applied to each amplifying circuit is preferably substantially equal for each circuit. This creates a substantially uniform electric field of the same value between the electrodes of each capacitor.

Where a number of amplifying circuits are used, one electrode of each capacitor may be provided by a common plate.

In a second embodiment one amplifying circuit is provided which scans across the article producing signals which are then sequentially fed directly to the processing unit before being displayed.

If the article comprises a metallic layer then preferably one of the capacitor plates is provided by the metallic layer of the article.

In any of the embodiments one electrode of the capacitor could be formed from a matrix of electrode pads connected electrically and configured to the shape of the article to be detected.

The monitoring techniques and apparatus described above are particularly advantageous when monitoring the composition of articles where the thickness of the article is of the same order as the required resolution. This is typically of about 1 mm to 5 mm.

BRIEF DESCRIPTION OF THE DRAWINGS

Three examples of monitoring apparatus in accordance with the present invention will now be described with reference to the accompanying drawings, in which.

DETAILED DESCRIPTION OF THE EMBODIMENTS

Figure 1:
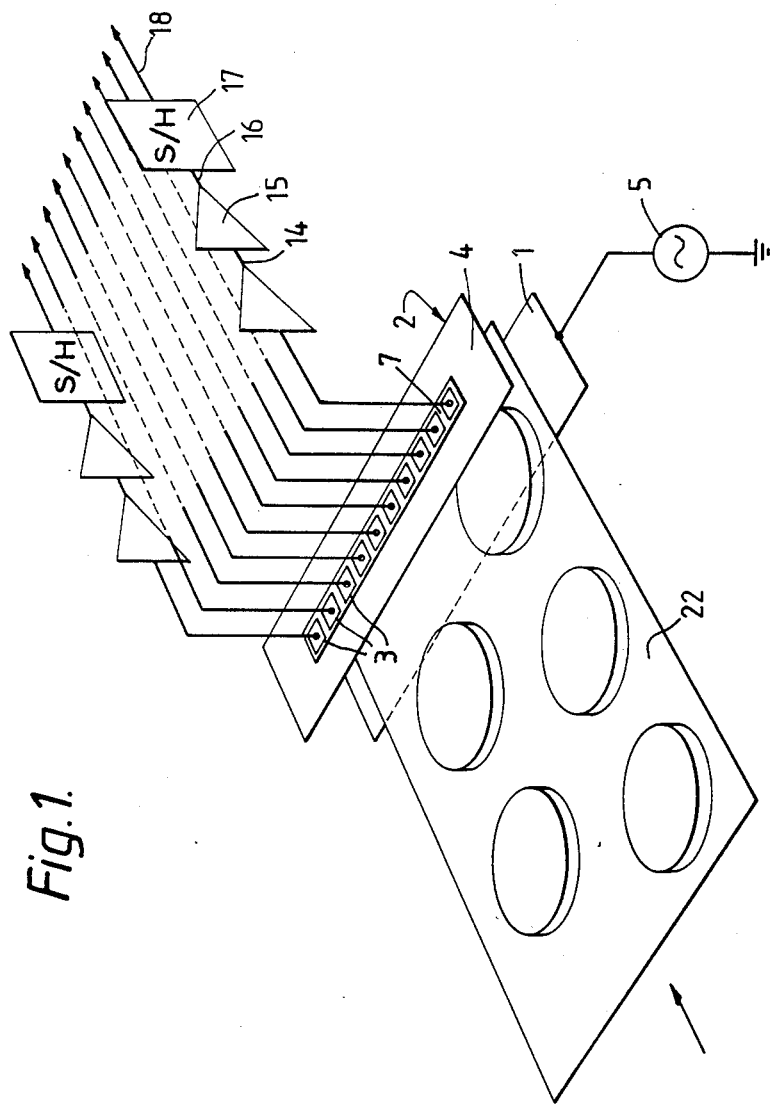
FIG. 1 is a schematic perspective view of a first example of the apparatus.

The apparatus shown in FIG. 1 comprises a continuous electrode 1 and an electrode assembly 2 which includes a number of sensing electrodes 3 and a guard electrode 4. The electrodes 1 and 2 are arranged so that their planar surfaces are parallel to each other. Thus each sensing electrode 3 in effect forms a capacitor with the continuous electrode 1. An oscillating voltage signal (typically 10 V peak to peak) is applied to the continuous electrode 1 by an oscillating voltage source 5 so that the whole of the electrode 1 is at a uniform potential at any instant in time. The guard electrode 4 on the electrode 2 is kept at a constant potential, which can be conveniently achieved by connecting it to an electrical ground potential 6 as shown in the circuit diagram of FIG. 3.

Figure 3:
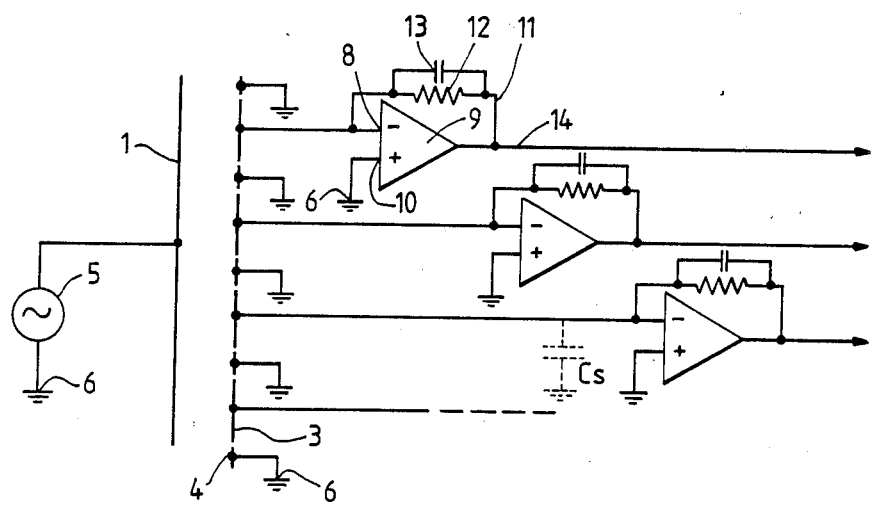
FIG. 3 is a circuit diagram of the apparatus shown in FIG. 1.

The sensing electrodes 3 are electrically isolated from the guard electrode 4 by an electrically insulating material 7. Each sensing electrode 3 is electrically connected to the inverting input 8 of a respective operational amplifier 9 forming part of an amplifying circuit as shown in FIG. 3 and the non-inverting input 10 of the operational amplifier 9 is electrically connected to the ground potential 6. A feedback loop 11, including a resistor 12 (typically 10MΩ) and a capacitor 13 (typically pF) connected in parallel, is connected between the output 14 of the operational amplifier 9 and the inverting input 8. This feedback loop has the effect of forcing the inverting and the non-inverting inputs 8, 10 to the same potential and as the non-inverting input is at ground potential, the inverting input is also at ground potential. Thus the sensing electrodes 3 are all effectively at ground potential.

Because the guard electrode 4 and the sensing electrodes 3 are all at the same potential (i.e. ground), a uniform electric field is created between the electrodes 1, 2.

The outputs 14 of the amplifiers 9 are each connected to respective peak detectors 15 which in turn are connected to respective sample and hold circuits 17.

Figure 2:
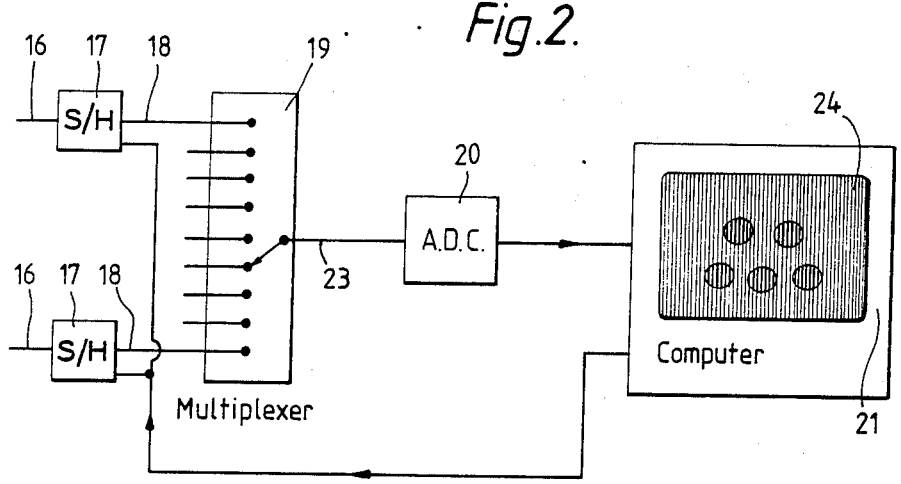
FIG. 2 is a schematic diagram of the processing and display apparatus used in conjunction with the apparatus shown in FIG. 1.

The outputs 18 from the sample and hold circuits 17 are each connected to a common multiplexer 19 (FIG. 2) which is in turn connected to an analogue to digital converter 20. The analogue to digital converter 20 is connected to a processing unit or computer 21 and a display 24.

In use an article 22, in this example a blisterpack containing pills is passed between the electrodes 1, 2. The capacitance between the sensors 3 and the electrode 1 is dependent on the dielectric constant of the article between the sensors 3 and the electrode 1, and therefore changes as the blisterpack passes through the electrodes 1, 2 due to the presence or absence of pills within the blisterpack pockets. As an oscillating voltage signal is applied to the electrode 1 a corresponding capacitance signal is induced on each sensing electrode 3, and this signal is representative of the dielectric constant between each sensing electrode 3 and the electrode 1. The peak value of the output signal 14 from each amplifier 9 varies directly with the dielectric constant between the sensing electrode 3 to which it is connected and the electrode 1.

The output signal 14 is then fed to the peak detector 15 which senses the maximum of the output signal 14 at regular intervals and provides a corresponding maximum value output signal 16 which varies directly with the dielectric constant of the article. The output signal 16 from the peak detector 15 is then fed via the sample and hold circuit 17 to the multiplexer 19. The output 23 of the multiplexer 19 is continuously cycled through all of the outputs 18 from the sample and hold circuits 17 and this output 23 is then fed to the analogue to digital converter 20. The analogue to digital converter 20 converts the analogue peak voltage signals to digital signals and then feeds these digital signals to the processing unit 21. The cycling of the multiplexer inputs is duplicated by the raster display on the monitor 24 which then displays an image of the variation in dielectric constant as the blisterpack is moved between the electrodes 1, 3.

As the signal from any one of the electrodes 3 will contain signal contributions not only from the material directly underneath that electrode but also from material under adjacent electrodes a resulting image produced from these signals could be blurred. In order to remove this blurring of the image a deconvolution operation is performed on the signals by the processing unit 21. The process of deconvolution is well known in digital image processing and only a brief description of the procedure is given below. A detailed description of the procedure can be found in "Fourier Transforms and their Physical Applications" by D. C. Champeney and published by Academic Press.

An image of a single small column of dielectric material can be denoted generally by the function $h(g,k)$. If a distribution of dielectric material is $d(j,k)$ then the image of the distribution will be $i(j,k)$ where $i(j,k) = h(j,k) * d(j,k)$ and "*" denotes the well known convolution operation. To produce an image with reduced blur we need to solve the above equation for $d(j,k)$ the actual, nonblurred, representation of the distribution of dielectric. This can be done as follows, by first taking the fourier transform of both sides of the above equation. Thus $i(j,k) = h(j,k) * d(j,k)$ becomes $I(u,v) = H(u,v) D(u,v)$ where u and v are angular spatial frequencies. Therefore $D(u,v) = I(u,v)/H(u,v)$. By taking the inverse fourier transform of this equation we get $d(j,k) = i(j,k) * F^{-1}(1/H(u,v))$ where $F^{-1}$ denotes the inverse fourier transform. $F^{-1}(1/H(u,v))$ is a two dimensional function which can be denoted as $f(j,k)$.

Thus the required unblurred function $d(j,k)$ is given by the following expression $d(j,k) = i(j,k) * f(j,k)$ where $f(j,k) = F^{-1}(1/H(u,v))$.

After this process of deconvolution has been carried out on the blurred image to produce a nonblurred image the nonblurred image of the article 22 is displayed on a screen 24. An operator can then determine from the displayed image whether there are any broken or missing pills in the blisterpack.

Figure 4:
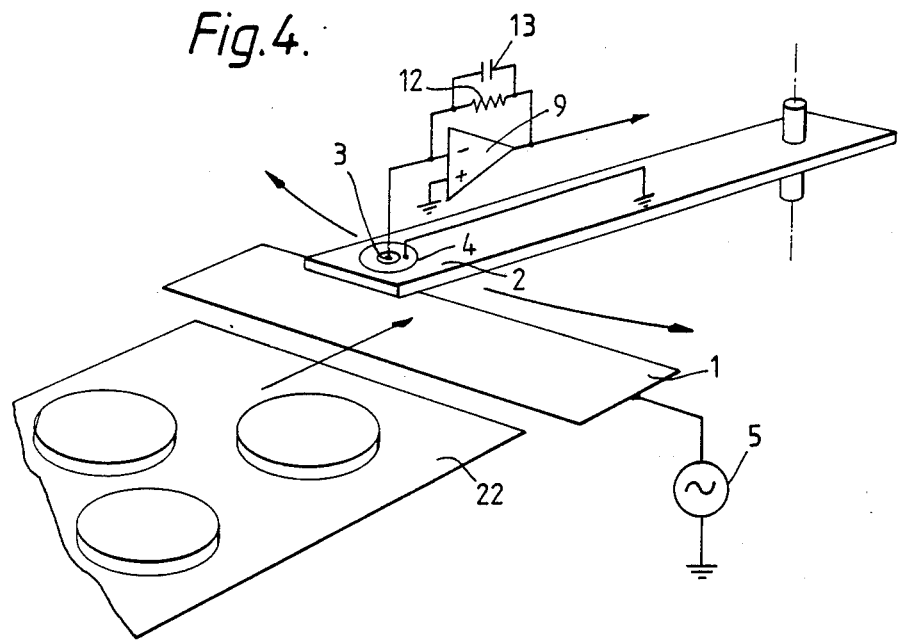
FIG. 4 is a schematic perspective view of a second example of the apparatus.

The apparatus shown in FIG. 4 operates on the same principles as the apparatus shown in FIG. 1 the difference between the two examples being that in FIG. 4 only a single sensing electrode 3 is used instead of a number of sensing electrodes 3. Therefore there is only one amplifier 9, one peak detector 15 and one sample and hold circuit 17. Thus the output 18 from the sample and hold circuit 17 can be connected directly to the analogue to digital converter 20 without the use of a multiplexer 19. In use an oscillating voltage signal is applied by the oscillator 5 to the continuous electrode 1 as before and an article 22 is passed between the continuous electrode 1 and the sensing electrode 3. As the article 22 passes between the two electrodes 1, 3 the sensing electrode 3 is scanned backwards and forwards across the article 22 to produce output signals which are representative of the dielectric constant of the article and these are then processed using the deconvolution procedure in the processing unit 21 and imaged on the screen 24 as before.

Figure 5:
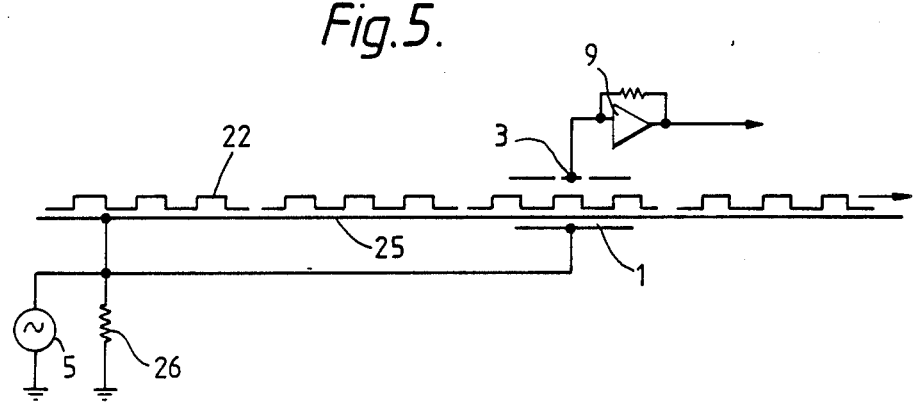
FIG. 5 is a schematic side view of a third example of the apparatus.

The apparatus shown in FIG. 5 can be used with either the apparatus in FIG. 4 or the apparatus in FIG. 1. In this example the article 22 is again a blisterpack but this time with a metallic backing foil 25. Because the metallic backing foil 25 is a conductor a potential applied to the continuous electrode 1 would be screened from the sensing electrode 3 by the backing foil 25. Hence the oscillating voltage must be applied to the backing foil 25 of the blisterpack 22. Thus the backing foil 25 acts as the continuous electrode 1. The voltage applied to the foil 25 would typically be 10 volts peak to peak and as the foil would be grounded to earth via a 10 ohm resistor 26 there would be no danger of electrocution while using this apparatus. The amplifier 9 and the other components of the detecting apparatus are identical to that used in the apparatus shown in FIGS. 1 and 4.

Figure 6:
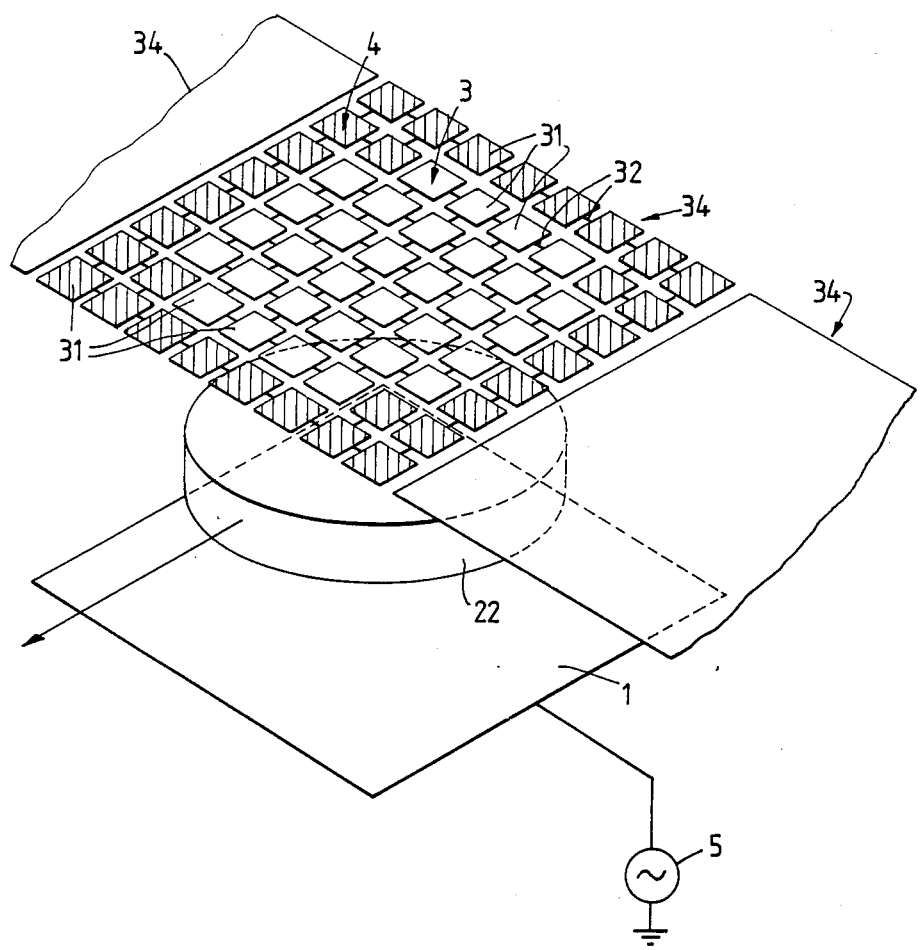
FIG. 6 is a schematic perspective view of a configured electrode for use with any of the examples.

In FIG. 6 the electrode 3 is a configured electrode which comprises a matrix of individual sensing pads 31 which form part of a sensing head 34. Each sensing pad 31 which forms part of the configured electrode 3 is electrically connected to its neighbors by a connection 32. The guard electrode 4 in this example also comprises a number of individual sensing pads 31 on the sensing head 34 which are again electrically connected to each other by means of connections 32. None of the connections 32 connect the sensing pads 31 of the guard electrode 4 to the sensing pads 31 of the configured electrode 3. Hence, the configured electrode 3 is electrically isolated from the guard electrode 4.

In the example shown in FIG. 6, the guard electrode 4 comprises the cross hatched pads, that is the four sensing pads 31 at each corner of the sensing head 34 and the peripheral pads of the sensing head 34, between the four pads of each corner of the sensing head 34. The configured electrode 3 is formed from the remainder of the pads 31, that is all the pads 31 except for the cross hatched pads, which are the four pads at each corner and the pads which form the periphery of the sensing head 34.

Preferably, the connections 32 are removable so that the configuration of the configured electrode 3 may be modified to suit a particular application. The configured electrode 3 could be configured to the same shape as the article 22 to be monitored by positioning the connections 32 appropriately.

Alternatively, the electrode 3 could be configured so as to be narrower than the article 22 in the direction of the third of the article 22 but have the same width as the article 22 in the direction perpendicular to the direction of the third. This would give better resolution of the articles 22 by the apparatus.

With these types of configured electrode it is only necessary to have one amplifier 9, one peak detector 15 and one sample and hold circuit 17 for each configured electrode 3. However, there could be more than one configured electrode 3. Where it is necessary to have a large sensing electrode it is possible to assemble a number of heads 34 in order to obtain a single configured electrode 3.

The type of configured electrode shown in FIG. 6 is particularly suitable for the detection of large multiple products such as biscuits in packs.

The advantages of using this apparatus and in particular the sensing circuit and amplifying circuit shown in FIG. 3 are that because the sensing electrodes 3 are all held at the same potential stray capacitances which may be present nearby do not affect the sensitivity or resolution of the apparatus. In addition this circuit is found to be very accurate and capable of detecting differences in capacitance of the order of $10^{-3}$ pF when the average capacitance present is of the order $10^{-2}$ pF. The surface area of the sensing electrodes 3 is typically 0.04 cm$^2$ and this will give a resolution of 2 mm when the top surface of the article is 2 mm from the sensing electrodes 3 and the thickness of the article is of the same order as the resolution. As the resolution of the article 22 decreases as the article moves further away from the sensing electrodes 3 the apparatus and circuit described here are also capable of monitoring the surface topology of an article.

Although the article 22 in the three examples was a blisterpack, the apparatus may also be used for monitoring laminated board for bonding problems and reading digitised bar codes.

I claim:

1. Monitoring apparatus comprising an amplifying circuit which generates an output signal, said amplifying circuit including a capacitor defined by two electrodes between which an article is moved in use and in which the gain of said amplifying circuit varies with the capacitance of said capacitor so that the peak value of said output signal from said amplifying circuit varies with the dielectric constant of said article between said capacitor electrodes; and further comprising a peak detecting circuit which receives said output signal from said amplifying circuit and outputs a signal representing said peak values of said output signal generated by said amplifying circuit; and means for monitoring said signal from said peak detecting circuit so as to enable the magnitude of the dielectric constant of said article to be monitored.

2. Apparatus according to claim 1, wherein said amplifying circuit further comprises an operational amplifier having an inverting input, a non-inverting input and an output, said non-inverting input of said operational amplifier being connected to a constant electrical potential and said inverting input being connected to one electrode of said capacitor.

3. Apparatus according to claim 2, wherein said constant electrical potential is ground potential.

4. Apparatus according to claim 2, wherein the electrode of said capacitor not connected to said inverting input of said operational amplifier is connected to an oscillating signal source.

5. Apparatus according to claim 4, wherein said capacitor electrode connected to said oscillating signal source comprises a conducting layer formed on the opposite side of said article from said capacitor electrode connected to said inverting input of said operational amplifier.

6. Apparatus according to claim 2, further comprising a feedback loop connected between said output of said operational amplifier and said inverting input of said operational amplifier, whereby said inverting input is forced to substantially the same potential as said constant electrical potential.

7. Apparatus according to claim 1, wherein said means for monitoring comprises a processing unit for processing output signals from said amplifying circuit and a display device to display said signals processed by said processing unit.

8. Apparatus according to claim 7, wherein one amplifying circuit is provided which moves across said article transverse to the direction of motion of said article in use to produce signals which are then sequentially fed to said processing unit before being displayed.

9. Apparatus according to claim 1, wherein there is a plurality of amplifying circuits, each having substantially the same gain when the capacitance of each of the respective capacitors is substantially equal; and a multiplexer to which output signals from said amplifying circuits are sent.

10. Apparatus according to claim 9, wherein said respective capacitors are positioned in a line transverse to the direction of motion of said article in use.

11. Apparatus according to claim 2, wherein there is a plurality of amplifying circuits, each having substantially the same gain when the capacitance of each of the respective capacitors is substantially equal; and a multiplexer to which output signals from said amplifying circuits are sent; said constant electrical potential for each amplifying circuit being substantially equal.

12. Apparatus according to claim 9, wherein one set of said respective capacitor electrodes form a single, continuous electrode.

13. Apparatus according to claim 2, said apparatus further comprising a guard electrode in close proximity to said capacitor electrode connected to said inverting input of said operational amplifier, wherein said guard electrode is at substantially said same constant potential as said non-inverting input of said operational amplifier.

14. Apparatus according to claim 1, wherein one electrode of the capacitor is a matrix of electrode pads.

* * * * *